US008465788B2

(12) United States Patent
Ekhart et al.

(10) Patent No.: US 8,465,788 B2
(45) Date of Patent: Jun. 18, 2013

(54) ARABINOXYLANS FOR MODULATING THE BARRIER FUNCTION OF THE INTESTINAL SURFACE

(75) Inventors: Peter Frank Ekhart, Zwijnaarde (BE); Hans Van Der Saag, Brussels (BE); Sam Possemiers, Ghent (BE); Pieter Van Den Abbeele, Ghent (BE); Tom Van De Wiele, Ghent (BE); Audrey Martine Neyrinck, Louvain-la-Neuve (BE); Nathalie Maria Nelly Delzenne, Louvain-la-Neuve (BE); Patrice D Cani, Louvain-la-Neuve (BE)

(73) Assignee: BioActor B.V., Maastricht (NL)

( * ) Notice: Subject to any disclaimer, the term of this patent is extended or adjusted under 35 U.S.C. 154(b) by 0 days.

(21) Appl. No.: 13/059,293

(22) PCT Filed: Aug. 18, 2009

(86) PCT No.: PCT/EP2009/060669
§ 371 (c)(1),
(2), (4) Date: Oct. 10, 2011

(87) PCT Pub. No.: WO2010/020639
PCT Pub. Date: Feb. 25, 2010

(65) Prior Publication Data
US 2012/0230955 A1    Sep. 13, 2012

(30) Foreign Application Priority Data

Aug. 18, 2008  (GB) .................................. 0814980.9
Oct. 17, 2008  (GB) .................................. 0819034.0
Jul. 1, 2009   (GB) .................................. 0911406.7

(51) Int. Cl.
*A23G 3/00*  (2006.01)

(52) U.S. Cl.
USPC ........................................... 426/658; 514/54

(58) Field of Classification Search
USPC .......................................... 426/658; 514/54
See application file for complete search history.

(56) References Cited

U.S. PATENT DOCUMENTS

| | | | |
|---|---|---|---|
| 5,827,531 | A | 10/1998 | Morrison et al. |
| 6,558,930 | B2 | 5/2003 | Hwang et al. |
| 2004/0234672 | A1* | 11/2004 | Delcour .......................... 426/635 |
| 2009/0304852 | A1* | 12/2009 | Hopkins et al. ...................... 426/2 |
| 2010/0303953 | A1* | 12/2010 | Hamaker et al. .................... 426/2 |
| 2011/0020498 | A1* | 1/2011 | Broekaert et al. ................. 426/71 |
| 2012/0052152 | A1* | 3/2012 | Armentrout ........................ 426/2 |

FOREIGN PATENT DOCUMENTS

| | | |
|---|---|---|
| JP | 5112455 A | 5/1993 |
| JP | 2002322079 A | 11/2001 |
| JP | 2007268659 A | 10/2007 |
| WO | 94/02874 | 2/1994 |
| WO | 99/61036 | 12/1999 |
| WO | 2006/000027 A1 | 1/2006 |
| WO | 2006/002495 A1 | 1/2006 |
| WO | 2009/040445 A2 | 4/2009 |

OTHER PUBLICATIONS

Charalampopoulos D. et al. Application of Cereals and Cereal Components in Functional Foods: A Review. International J of Food Microbiology 79:131-141, 2002.*
Grootaert C. et al. Microbial Metabolism and Prebiotic Potency of Arabinoxylan . . . Trends in Food Science & Technology 18(2)64-71, Feb. 2007.*
Lu Z. et al. Arabinoxylan Fibre Improves Metabolic Control in People with Type II Diabetes European J of Clinical Nutrition 58:621-8, 2004.*
Vardakou M. et al. Evaluation of the Prebiotic Properties of Wheat Arabinoxylan Fractions . . . Int J of Food Microbiology 123(1-2)166-170, Mar. 2008.*
Lu Z. et al. Arabinoxylan Fibre, A Byproduct of Wheat . . . Am J Clinical Nutrition 71:1123-8, 2000.*
Van Craeyveld V. et al. Structurally Different Wheat Derived Arabinoxyloliogosaccharides . . . The J of Nutrition 138(12)2348-55, Dec. 2008.*
Grootaert C. et al. Arabinoxylan Oligosaccharides with Different Structures Exert a Bifidogenic Effect in a Mixed Intestinal Community Communications in Agricultural and Applied Biological Sciences 71(1)159-163, 2006.*
International Preliminary Report on Patentability for Application No. PCT/EP2009/060669 dated Nov. 10, 2010.
Backhed, F. et al.; The gut microbiota as an environmental factor that regulates fat storage; PNAS; Nov. 2, 2004; pp. 15718-15723; vol. 101; No. 44.

(Continued)

*Primary Examiner* — Ralph Gitomer
(74) *Attorney, Agent, or Firm* — Dinsmore & Shohl LLP

(57) ABSTRACT

The present invention is directed to a particular arabinoxylan ("AX") preparation and the finding that this preparation has a beneficial effect on the organization of the intestinal microbial community in the lumen and in particular at the site of the gut mucosa, where it modulates the barrier function of the intestinal surface, primarily by modulating the mucosa-associated microbial community towards a relative increase of health beneficial bacteria, such as bifidobacteria and lactobacilli. It is accordingly a first aspect of the present invention to provide said arabinoxylan preparation characterized in comprising isolated water-soluble arabinoxylans and the use thereof to improve functioning (e.g. barrier function) of the intestinal epithelium. Thus, in a further aspect the present invention provides compositions, both pharmaceutical and nutritional compositions, comprising said arabinoxylan preparations; in particular pharmaceuticals, medical foods, food supplements or food compositions, such as infant formula products, dairy products, bakery products or pastry products. The compositions optionally comprise probiotics such as *Bifidobacterium* or *Lactobacillus*.

9 Claims, 9 Drawing Sheets

OTHER PUBLICATIONS

Berg, D. et al.; Enterocolitis and Colon Cancer in Interleukin-10-deficient Mice Are Associated with Aberrant Cytokine Production and CD4+ TH1-like Responses; J. Clin. Invest.; Aug. 1996; pp. 1010-1020; vol. 98; No. 4; The American Society for Clinical Investigation, Inc.

Cani, P. et al.; Gut microflora as a target for energy and metabolic homeostasis; Current Opinion in Clinical Nutrition and Metabolic Care; 2007; pp. 10:729-734; Walters Kluwer Health/Lippincott Williams & Wilkins.

Courtin, C.M. et al.; Determination of reducing end sugar residues in oligo- and polysaccharides by gas-liquid chromatography; Journal of Chromatography A; 2000; pp. 97-104; vol. 886; Elsevier Science B.V.

Cummings, J.H. et al.; Role of intestinal bacterial in nutrient metabolism; Clinical Nutrition; 1997; pp. 3-11; vol. 16; Pearson Professional Ltd.

Delzenne, N. et al.; Modulation of Glucagon-like Peptide 1 and Energy Metabolism by Inulin and Oligofructose: Experimental Data; The Journal of Nutrition; 2007; pp. 2547S-2551S; American Society for Nutrition.

Freitas, M. et al.; Microbial Modulation of Host Intestinal Glycosylation Patterns; Microbial Ecology in Health and Disease; 2000; pp. 165-178; Suppl 2; Taylor & Francis.

Garcia, A.L. et al.; Arabinoxylan Fibre Consumption Improved Glucose Metabolism, but did not Affect Serum Adipokines in Subjects with Impaired Glucose Tolerance; Horm Metab Res; 2006; pp. 761-766; vol. 38; Georg Thieme Verlag KG Stuttgart.

Gibson, G. et al.; Dietary Modulation of the Human Colonic Microbiota: Introducing the Concept of Prebiotics; The Journal of Nutrition; 1995; 1401-1412; vol. 125; American Institute of Nutrition.

Glei, M. et al.; Both Wheat (*Triticum aestivum*) Bran Arabinoxylans and Gut Flora-Mediated Fermentation Products Protect Human Colon Cells from Genotoxic Activities of 4-Hydroxynonenal and Hydrogen Peroxide; Journal of Agricultural and Food Chemistry; 2006; pp. 2088-2095; vol. 54; American Chemical Society.

Grasten, S. et al.; Effects of wheat pentosan and inulin on the metabolic activity of fecal microbiota and on bowel function in healthy humans; Nutritional Research; 2003; pp. 1503-1514; vol. 23; Elsevier Inc.

BioActor and Jaeckering sign Joint Development & Marketing Agreement on wheat; Press Release; Dec. 1, 2005.

Lu, L. et al; Pathologic and physiologic interactions of bacterial with the gastrointestinal epithelium; Am J Clin Nutr; 2001; pp. 1124S-30S; vol. 73(suppl); American Society for Clinical Nutrition.

MacFarlane, G.T. et al; Human Colonic Microbiota: Ecology, Physiology and Metabolic Potential of Intestinal Bacteria; Scandinavian Journal of Gastroenterology; 1997; pp. 3-9; vol. 32 (Suppl 222).

MacFarlane, G. et al.; Models for intestinal fermentation: association between food components, delivery systems bioavailability and functional interactions in the gut; Current Opinion in Biotechnology; 2007; pp. 156-162; vol. 18; ScienceDirect.

Maes, C. et al.; Structural Characterisation of Water-extractable and Water-unextractable Arabinoxylans in Wheat Bran; Journal of Cereal Science; 2002; pp. 315-326; vol. 35; Elsevier Science Ltd.

Molly, K. et al; Development of a 5-step multi-chamber reactor as a simulation of the human intestinal microbial ecosystem; Applied Microbiology and Biotechnology; 1993; pp. 254-258; vol. 39; Springer-Verlag.

Neish, Andrew S.; The gut microfora and intestinal epithelial cells: a continuing dialogue; Microbes and Infection; 2002; pp. 309-317; vol. 4; Elsevier SAS.

Possemiers, S. et al.; PCR-DGGE-based quantification of stability of the microbial community in a simulator of the human intestinal microbial ecosystem; FEMS Microbiology Ecology; 2004; pp. 495-507; vol. 49; Elsevier B.V.

Reinert, Birgit; Friendly tenants in the human gut: The genome of B. longum; Genome News Network; Oct. 25, 2002.

Rose, D. et al.; Influence of Dietary Fiber on Inflammatory Bowel Disease and Colon Cancer: Importance of Fermentation Pattern; Nutrition Reviews; Feb. 2007; pp. 51-62; vol. 65; No. 2; International Life Sciences Institute.

Seifert, S. et al.; Inulin and Oligofructose: Review of Experimental Data on Immune Modulation; The Journal of Nutrition; 2007; pp. 2563S-2567S; vol. 137; American Society for Nutrition.

Van Craeyveld, V. et al.; Structurally Different Wheat-Derived Arabinoxylooligosaccharides Have Different Prebiotic and Fermentation Properties in Rats; The Journal of Nutrition; Dec. 1, 2008; pp. 2348-2355; vol. 138; No. 12; American Society for Nutrition.

International Search Report dated Dec. 22, 2009 pertaining to International application No. PCT/EP2009/060669.

Courtin, C.M. et al; Physicochemical and Bread-Making Properties of Low Molecular Weight Wheat-Derived Arabinoxylans; J. Agric. Food Chem. 1998, pp. 4066-4073, 46; American Chemical Society.

\* cited by examiner 28 min = 8 kDa
24 min = 20 kDa

| Component | Content (%) on d.m. |
|---|---|
| Starch | 48,2% |
| Glucose | 2,7% |
| Pentosans | 14,7% |
| ß-glucan | 0,7% |
| Protein | 12,1% |
| Ash | 2,6% |
| Fat | 1,5% |

| Component | Content (%) on d.m. |
|---|---|
| Starch | 5,7% |
| Glucose | 0,5% |
| Arabinoxylan | 60,0% |
| Arabinogalactan | 25,0% |
| ß-glucan | 0,7% |
| Protein | 5,0% |
| Ash | 2,6% |
| Fat | 0,5% |

ARABINOXYLANS FOR MODULATING THE BARRIER FUNCTION OF THE INTESTINAL SURFACE

This application is a National Stage application filed under Rule 371 based upon PCT/EP09/60669 filed Aug. 18, 2009 which claims benefit of priority to UK application 0911406.7 filed Jul. 1, 2009 which claims benefit of priority to UK application 0819034.0 filed Oct. 17, 2008 which claims benefit of priority to UK application 0814980.9 filed Aug. 18, 2008.

FIELD OF THE INVENTION

The present invention is directed to a particular arabinoxylan ("AX") preparation, hereinafter also referred to as NAXUS and the finding that this preparation has a beneficial effect on the organization of the intestinal microbial community in the lumen and in particular at the site of the gut mucosa, where it modulates the barrier function of the intestinal surface, primarily by modulating the mucosa-associated microbial community towards a relative increase of health beneficial bacteria, such as bifidobacteria and lactobacilli. This invention further covers methods for the production of AX preparations, as well as certain AX preparations and compositions.

It is accordingly a first aspect of the present invention to provide said arabinoxylan preparation characterized in comprising isolated long-chain water-soluble arabinoxylans and the use thereof to modulate the attachment of non-pathogenic bacteria to the mucosal layer of the gastrointestinal epithelium and the interaction of these bacteria with the epithelium. This may lead to improved functioning (e.g. barrier function) of the intestinal epithelium.

Thus, in a further aspect the present invention provides compositions, both pharmaceutical and nutritional compositions, comprising said arabinoxylan preparations; in particular pharmaceuticals, medical foods, food supplements or food compositions, such as infant formula products, dairy products, bakery products or pastry products. The compositions optionally comprise probiotics such as *Bifidobacterium* or *Lactobacillus*.

BACKGROUND TO THE INVENTION

The human gut ecosystem consists of a variety of different habitats and metabolic niches that are colonised by the so-called microbiota that contain more than $10^{11}$ micro-organisms per gram wet weight of contents, predominantly anaerobes (Macfarlane et al. 1997). The intestinal microbiota have both beneficial and pathogenic potential (Fuller & Gibson, 1997). The microbial community can provide protection against pathogenic bacteria, stimulates cell-mediated and humoral immune responses, and indirectly supports digestive processes by microbial fermentation (Berg, 1996; Cummings & Macfarlane, 1997). It also includes potential pathogenic organisms such as certain species of *Clostridium, Escherichia, Salmonella, Shigella* and *Pseudomonas*, as well as yeasts such as *Candida albicans* (Salminen et al. 1995). Evidence exists that the best protection against mucosal attachment and invasion by such pathogens is by keeping intestinal microbiota in a state that affords colonisation resistance against pathogens by modulation of the microbiota and by inducing luminal or systemic effects which are beneficial to the host's health. This may be achieved by the consumption of non-digestible food ingredients such as inulin-type fructans, known as prebiotics, which favour the growth and activity of certain colonic bacteria, such as bifidobacteria and lactobacilli, generally regarded as beneficial to the host.

However, not only the composition of the microbiota, but also the interaction of bacteria with the mucus layer and/or with the intestinal mucosa is important. The mucus layer is formed by high-molecular-weight mucins secreted by the goblet cells, secretory proteins and polymers mainly composed of polysaccharides. In addition, other glycoconjugates are also present; mainly glycoproteins and glycolipids synthesised by most of the epithelial cells producing the glycocalyx (Freitas & Cayuela, 2000). While these mucins and polymers may form a barrier against colonisation by some bacteria, other bacteria can use them as a means to adhere to the surface. Adherence leads to the formation of an adhesive microbial layer of one species that subsequently may support colonisation of other micro-organisms through co-adherence, promoting the development of microcolonies and biofilms.

It is accordingly, the combination of an intact intestinal mucosa covered with a biofilm of non-pathogenic bacteria that represents a barrier to the unrestrained uptake of antigens and pro-inflammatory molecules, including bacteria and bacterial products. When the normal microbiota, the mucus layer or the epithelial cells are disturbed by pathogens, antigens and other toxic substances from the gut lumen, defects in the barrier system become evident (Neish, 2002). Such a compromised mucosal barrier may increase paracellular permeability of the mucosa. As a consequence, the probability of an invasion by bacteria, antigens and pro-inflammatory molecules of the intestinal mucosa is increased under these conditions, resulting in inflammatory and immunologic responses (Lu & Walker, 2001). Because the first contact of bacteria with the intestinal tissue is with the mucus layer, which covers the underlying epithelium, consisting of enterocytes, columnar in shape, with an apical and a basolateral side and microvilli on the apical side, it represents an important element in the first line of defense against the invasion by pathogens, antigens or other harmful substances.

Therefore, the best protection against mucosal attachment and invasion by pathogens or other harmful substances could be the maintenance of the normal microbiota adhering tenaciously to mucus overlaying the mucosa. It is an object of the present invention to provide particular preparations useful in realizing the above, i.e. maintaining and/or improving the adherence of the normal microbiota to the mucosal layer.

In another aspect, more and more scientific data indicate that the intestinal microbiota impacts energy and metabolic homeostasis of the host, i.e. control of food and energy intake, food and energy metabolism, fat mass development, and associated metabolic disorders such as obesity and type 2 diabetes (Cani and Delzenne, 2007). Several mechanisms are now proposed that link events occurring in the colon and the regulation of energy metabolism. Intuitively, the major part of the microbiota is present at a point in the gut where food products escaped host digestion. By using these products, they intervene in host metabolism to provide energy through the production of metabolites absorbed by colonic host cells (short chain fatty acids). But they intervene also through more indirect ways. The following, non-limiting list of mechanisms may play an important role in metabolic homeostasis:

Propionate is a microbial metabolite which reduces cholesterol and triglyceride synthesis (Delzenne, 2007).

Impact of the gut microbiota on the fasting-induced adipose factor (FIAF) in the gut, which inhibits the activity of the enzyme lipoprotein lipase (LPL) (Backhed, 2004). This enzyme controls the release of fatty acids in the muscles and adipose tissue.

Type 2 diabetes and obesity are closely associated to a low-tone inflammatory state in response to being fed a high-fat diet. The bacterial lipopolysaccharide (LPS) from the Gram-negative intestinal microbiota may play an important role in this process, as absorbed lipopolysaccharide triggers the secretion of proinflammatory cytokines when it binds to the complex of CD14/TLR4 at the surface of immune cells (Cani and Delzenne, 2007).

Modulation of the production of gut peptides could constitute a link between bacterial fermentation in the lower part of the gut and systemic consequences of "colonic food" intake (Delzenne, 2007). More in particular such peptides either directly act as hormones modulating downstream metabolic processes, or indirectly trigger the production of hormones modulating such processes. In addition to others, glucagon-like peptide-1 and -2 (GLP-1 and GLP-2) are key hormones released in response to nutrient ingestion. They are produced by processing of their precursor proglucagon and promote insulin secretion (and sensitivity) and b-cell proliferation in the pancreas, control glycogen synthesis in muscle cells, and promote satiety. An increase in proglucagon mRNA and GLP-1 or -2 levels in the proximal colon are key events in the interaction between gut microbiota and metabolic homeostasis of the host.

Arabinoxylan (AX), the main non-starch polysaccharide of cereal grains, is a dietary fiber constituent. These complex carbohydrates occur in cell walls of the starchy endosperm cells and the aleurone layer in most cereals (60-70% (w/w) of the total carbohydrate). They can be found in the endosperm cell walls of barley (20% (w/w)) and rice (40% (w/w)). Non-endospermic tissues of wheat, particularly the pericarp and testa, also contain a very high concentration of AX (64% (w/w)). AX consist of □-(1,4)-linked D-xylopyranosyl residues to which □-L-arabinofuranose units are linked as side chains (FIG. 1a). Some arabinoses can be substituted with ferulic acid. The degree of substitution refers to the arabinose moieties on the xylose backbone and is further also described as A/X ratio. The substitution and distribution of side chains are important factors in the physicochemical properties of AX. As for other polymers, also the degree of polymerization (DP), i.e. the molecular weight ratio of the polymer vis-à-vis the molecular weight of the repeating units, is an important factor in the physicochemical properties of AX. As used herein, the degree of polymerization is determined according to Courtin et al. (J. Chromatograph. A866 (2000) 97-104), i.e. measuring the number of reducing end xylose residues as repeating units.

AX are present in water-extractable form in grains and in a water-unextractable fraction present in the cell wall material. Whereas the latter one needs to be extracted from wheat using for instance alkali treatment, the water-extractable fraction is readily available in the watery waste streams from the wheat processing (Maes and Delcour 2002). In the current state of the art AX are extracted by using enzymes (i.e. hemicellulases and endoxylanases) which leads to (partial) hydrolysis of AX and results in a mixture of soluble and non-soluble AX molecules with low molecular weight (WO 199402874), (WO 2006027), (WO2006/002495), (U.S. Pat. No. 6,558,930). The reason for the focus on short chain—hydrolyzed—AX and the use of hemicellulases is that the yield of soluble long-chain AX is supposed to be too low. One reason for this low yield is the fact that endogenous enzymes are likely to degrade long-chain AX. Another reason is that the inherent viscosity of long-chain AX poses challenges for an efficient and cost effective extraction. It is also generally assumed that long-chain AX are badly water soluble because of their viscous nature. Finally, long-chain AX are not widely used for obtaining health/physiological effects, as it is currently assumed that only the short chain AX (soluble and non-soluble) have interesting physiological effects.

For all these reasons, the prior art describes the combined extraction of soluble and non-soluble AX with the aid of enzymes such as hemicellulases, endoxylanases etc resulting in short chain AX. Indeed, pre-biotic effects have so far only been described with AX of low molecular mass (see below).

There are also structural and functional differences that have been described between both soluble and non-soluble fractions (Glei, Hofmann et al. 2006). It is known from the literature (Garcia et al (2006) that long-chain AX have effects on glycaemic control in pre-diabetics, whilst such effects are not described for short chain AX.

The current invention surprisingly showed that: (i) methods are available that lead to acceptable yields of long chain soluble AX; (ii) hydrolysis or degradation of long-chain AX by the aforementioned enzymes can be largely avoided; (iii) long chain soluble AX have potent pre biotic and other systemic and non-systemic physiological effects, and (iv) the long chain AX preparations of the present invention have a good solubility profile.

Non digestible oligosaccharides (NDOs) like arabinoxylans, resist digestion and absorption in the human small intestine with complete or partial fermentation in the large intestine. These carbohydrates help to maintain regularity of colonic functions and could possibly contribute to human health by reducing the risk of chronic diseases. A lot of NDOs are considered to be prebiotics. Certain short chain arabinoxylans are also known to improve the growth of beneficial bacteria in the colon (WO2006002495 (A1), Grasten, 2003), (WO 2006/002495), however, no improved barrier function or selective growth and attachment of beneficial bacteria in the distal part of the colon were observed.

Prebiotics are non-digestible food ingredients that beneficially affect the host by selectively stimulating the growth and/or activity of one or a limited number of beneficial bacteria in the colon, thereby improving the host health (Gibson and Roberfroid 1995). Prebiotic effects in the gut can be evaluated on the basis of the growth of health promoting bacteria such as lactobacilli and bifidobacteria, the decrease in intestinal pathogens and the increase or decrease in production of health related bacterial metabolites. The latter include for instance short chain fatty acids, which are generally believed to be positive for colonic health, but also polyamines and ammonia, which are regarded as a risk factor for colon carcinogenesis.

DETAILED DESCRIPTION OF THE INVENTION

Figure 1A:
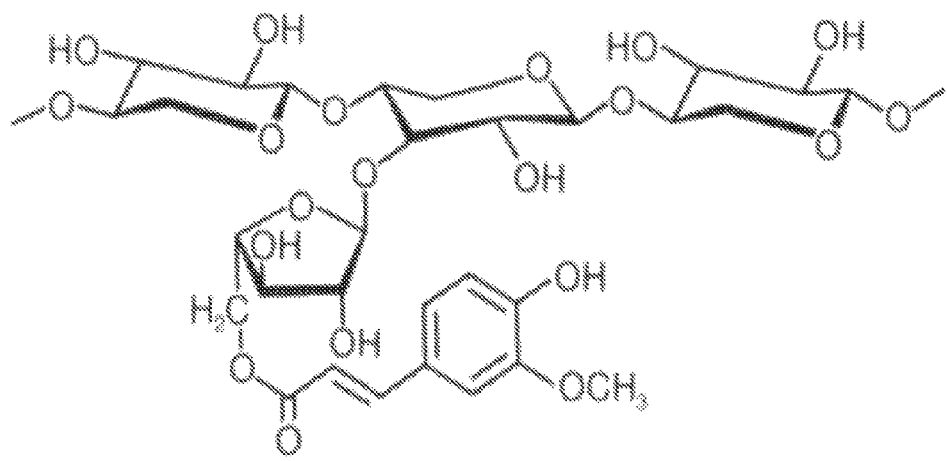
FIG. 1a The chemical structure of AX that consists of a backbone of xylose molecules with arabinose side chains and ferulic acid substitutions.

This invention relates to methods and compositions, i.e. comprising arabinoxylan preparations, for modulating the specific composition of the intestinal microbiota and the specific interaction of the human intestinal flora with the intestinal surface and the host.

In one embodiment of the present invention, the application of the arabinoxylan preparations as provided herein, results in a relative increase in the number of non-pathogenic bacteria attached to the intestinal surface, resulting in an enhanced interaction of these bacteria with the intestinal surface, leading to an improved functioning (e.g. barrier, hormonal, immune functioning) of the intestinal surface.

As used herein, modulating or improving the barrier, hormonal or immune function of the intestinal surface is meant to include altering any parameter that affects the normal homeostasis of the intestinal surface and in particular its role in the first line defense against the invasion by pathogens, antigens or other harmful substances and its role to produce substances (e.g. immune molecules, hormones) which have systemic influences on the host. Said parameters include, but are not limited to;

- a stimulation of the growth and/or activity of one or a limited number of beneficial bacteria in the intestinal tract (e.g. lactobacilli, bifidobacteria, butyrate- or propionate-producing bacteria, others);
- an inhibition of the growth and/or activity of one or a number of pathogenic bacteria in the intestinal tract;
- a relative increase in the attachment of non-pathogenic bacteria to the mucosa of the intestinal surface;
- a reduction in the uncontrolled uptake from the gut of antigens, pro-inflammatory molecules, bacteria or bacterial products;
- an anti-inflammatory activity at the intestinal surface and stimulation of the host immune system;
- production of specific bacterial metabolites (e.g. propionate, butyrate); and
- modulation of the production of certain intestinal signaling molecules that directly or indirectly modulate metabolic homeostasis (e.g. proglucagon, GLP-1, GLP-2, FIAF)

Based on the observation that the arabinoxylan preparations of the present invention enhance the interaction and/or activity of non-pathogenic bacteria to the mucosal layer of the gastrointestinal epithelium, it is to be envisaged that said preparations are particularly useful to improve the barrier function of the intestinal surface, such as for example to prevent or reduce the uncontrolled uptake from the gut of antigens, pro-inflammatory molecules, pathogenic bacteria or bacterial products. One such indication, with an impaired mucosal barrier is inflammatory bowel disease. As it is generally accepted that in inflammatory bowel diseases, mucosal injury with an impaired resolution of the lesions is one of the key elements that lead to these chronic indications, it is to be expected that the arabinoxylan preparations of the present invention, will have a beneficial effect in said indication. It is accordingly an objective of the present invention, to provide the use of the arabinoxylan preparations of the present invention in the prevention and treatment of conditions associated with an impaired barrier function and characterized by the uncontrolled uptake from the gut of antigens, pro-inflammatory molecules, pathogenic bacteria or bacterial products.

"Inflammatory bowel diseases" also referred to as "chronic colonic diseases", as used herein include any condition characterized by persistent mucosal inflammation at different levels of the gastrointestinal tract, such as for example inflammatory bowel syndrome, mucositis, gastric ulcers, Crohn's disease, ulcerative colitis, colorectal cancer and pouchitis.

It is also to be envisaged that the application of the arabinoxylan preparations would provide protection against invasion by antigens that cause allergic reactions, whereby such allergens may comprise certain food substances, chemicals and other molecules. Thus in a further embodiment, the present invention provides the use of the arabinoxylan preparations in the prevention and treatment of conditions associated with the invasion by antigens that cause allergic reactions (e.g. food allergies, asthma, eczema)

It is furthermore also to be envisaged that the application of the arabinoxylan preparations would influence both the gut-associated lymphoid tissue (GALT) as well as the systemic immune system. Among other effects this may result in decreased expression of proinflammatory cytokines and increased production of immunoregulatory factors and improved activity of lymphocytes (Seifert, 2007). It is therefore to be envisaged that said preparations are particularly useful in improving the development and functioning of the host immune system.

In another aspect of the invention, based on the observation that the arabinoxylan preparations modulate the production of certain intestinal signaling molecules that directly or indirectly modulate metabolic homeostasis (e.g. proglucagon, GLP-1, GLP-2, FIAF), it is to be envisaged that said preparations are particularly useful in controlling and improving metabolic homeostasis. Non-limiting effects of said preparations on metabolic homeostasis include control of food intake and fat and glucose metabolism, improvement of insulin secretion and sensitivity and control of cholesterol synthesis and metabolism. It is accordingly an objective of the present invention, to provide the use of the arabinoxylan preparations of the present invention in the management of food uptake, induction of satiety, weight management, the prevention and treatment of conditions associated with an impaired metabolic homeostasis, such as obesity and type 2 diabetes; and in improving the development and functioning of the host immune system (immune support).

Based on the observation that the arabinoxylan preparations of the present invention decrease several established causal risk factors of cardiovascular diseases (CVD), it is to be envisaged in another aspect of the invention that said preparations are particularly useful for the prevention and/or treatment of CVD. CVD technically refers to any disease that affects the cardiovascular system, yet is usually used to refer to those related to atherosclerosis. The latter is a syndrome affecting arterial blood vessels, a chronic inflammatory response in the walls of arteries, in large part due to the accumulation of macrophage white blood cells and promoted by low density lipoproteins. CVD development depends on multiple mechanisms and a number of clear causal risk factors have been identified. These factors include, yet are not limited to, elevated LDL cholesterol, plasma triglycerides, metabolic diseases (obesity, diabetes, . . . ), chronic inflammation and oxidative stress. Especially the latter two factors are of utmost importance. Atherosclerosis develops from LDL becoming oxidized (LDL-ox) by free radicals, particularly oxygen free radicals, in situations of oxidative stress. Excessive response of the immune system, in case of chronic inflammation, to damage caused by LDL-ox further promotes the expansion of the disease. Based on the observed protection against oxidative stress and the observed immune-modulatory and anti-inflammatory effect, it is accordingly an objective of the present invention, to provide the use of the arabinoxylan preparations of the present invention in the prevention and/or treatment of CVD.

In a further aspect, given the beneficial effect of the preparations of the present invention on the adherence of the normal microbiota to the mucosal layer, it is to be envisaged that the application of the arabinoxylan preparations would provide protection against mucosal attachment and invasion by pathogens, such as certain species of *Clostridium, Escherichia, Salmonella, Shigella* and *Pseudomonas*, as well as yeasts such as *Candida albicans*. Thus in a further embodiment, the present invention provides the use of the arabinoxylan preparations of the present invention in the prevention and treatment of conditions associated with the mucosal attachment and invasion by pathogens; in particular in the treatment and prevention of acquired diarrhoea and traveller's diarrhoea.

Where current prebiotics, such as fructo-oligosaccharides, galacto-oligosaccharides, short-chain xylo-oligosaccharides and inulin, are limited in their persistence to the distal colon and are predominantly active in the proximal part of the colon, the arabinoxylan preparations of the present invention exert their effect throughout the total colon, including the distal part of the colon. This finding is particularly important since most chronic colonic diseases (for example, ulcerative colitis and colorectal cancer) originate in the distal colon. It is accordingly a further aspect of the present invention, to provide the arabinoxylan preparations of the present invention as a prebiotic, in particular in the treatment of chronic colonic diseases, such as for example, ulcerative colitis and colorectal cancer.

The arabinoxylan preparations of the present invention contain the water-extractable AX fraction, and are characterized in comprising isolated water-soluble arabinoxylans with various chain lengths, having a weighted average molecular weight of at least 10 kDa, in particular having an average molecular weight fraction of about 15 kDa to 30 kDa; more in particular of about 8 kDa to about 20 kDA.

As cereals contain several enzymes that may degrade/hydrolyze AX and thus lead to AX molecules of low molecular weight, it was surprisingly found that the isolation of the water soluble AX fraction results in a mixture of AX molecules with a relatively high molecular weight. Therefore, in a further aspect the arabinoxylan preparations of the present invention are also characterized in having an average degree of polymerization of about 50 or higher; in particular an average degree of polymerization of about 75 or higher, more in particular having an average degree of polymerization of at least 100, even more in particular having an average degree of polymerization of about 150 to about 200. In one embodiment of the present invention, the arabinoxylan preparation of the present invention is characterized in having an average degree of polymerization in excess of 1000, i.e. of about 1500 to about 2000.

In further embodiments of the present invention, the arabinoxylan preparations of the present invention may further be characterized in having one or more of the following characteristics;

further comprising one or more carbohydrates selected from the group consisting of arabinose, xylose, glucose, galactose, mannose and rhamnose; in particular arabinose, xylose, galactose and glucose; more in particular arabinose and xylose.

containing at least 5% (w/w); in particular at least 15% (w/w); more in particular at least 30% (w/w) of arabinoxylans; more in particular at least 60% (w/w) of arabinoxylans; in particular about 55%-85% (w/w) of arabinoxylans.

having a protein content of up to about 5%, 10% or 15% (w/w); more in particular having a protein content of up to about 22% (w/w).

having a degree of substitution between 0.4 and 0.9, and more in particular at least 0.5; in particular a degree of substitution of 0.7

In a particular embodiment the arabinoxylan preparations of the present invention have a total sugar concentration of at least 50% (w/w); in particular about and between 50-85% (w/w); in particular having a sugar content of about 56% (w/w); wherein the sugar content typically consists of;

about 10 to 40% (w/w) of arabinose; more in particular about 15 to 30% (w/w); even more in particular about 25% of arabinose;

about 15 to 55% (w/w) of xylose; more in particular about 20 to 30% (w/w); even more in particular about 35% of xylose;

about 0-15% (w/w) of galactose; in particular about 9% of galactose;

about 1-10% (w/w) of glucose; in particular about 8% of glucose;

about 0-5.0% of (w/w) Mannose; in particular about 1% of Mannose; and about 0 to 1.0% of (w/w) Rhamnose; in particular about 0.5% of Rhamnose.

It is thus an object of the present invention to provide an arabinoxylan preparation characterized in;

having an average molecular weight of at least 8 kDa, in particular having an average molecular weight fraction of about 8 kDa to 30 kDa; more in particular of about 8 kDa to about 20 kDA;

having an average degree of polymerization of about 50 or higher; in particular an average degree of polymerization of about 60 or higher; more in particular an average degree of polymerization of about 75 or higher, even more in particular having an average degree of polymerization of at least 100, in an even further embodiment having an average degree of polymerization of about 150 to about 200;

having a degree of substitution between 0.4 and 0.9, and more in particular at least 0.5; in particular a degree of substitution of 0.7;

having a protein content of up to about 5%, 10% or 15% (w/w); more in particular having a protein content of up to about 22% (w/w); and containing at least 50% (w/w) of arabinoxylans; in particular about 55%-85% (w/w) of arabinoxylans.

In a particular embodiment, and as used in the examples hereinafter, the water-extractable AX fraction of the present invention, i.e. NAXUS, is produced from a watery side stream of starch production from wheat and as no alkali treatment is performed, the product only or predominantly contains the water-soluble AX fraction, with a molecular weight distribution ranging from about 10 kDa to about 1000 kDa, and an average molecular weight of approximately 20 to 30 kDa; in particular having an average molecular weight fraction of at least 8 kDa; more in particular of about 8 kDa to about 20 kDA.

This invention also provides for a novel method to produce any of the AX preparations envisaged in this invention. A water soluble AX product can be obtained from the wheat starch processing where a three phase decanter is employed to yield an A starch fraction, a gluten fraction and a third aqueous fraction named Hamino containing several components as summarized in FIG. 12. State of the art approaches to obtain purified water soluble AX include decanter and or separator treatments of the Hamino combined with selective enzymatic treatment by amylases and proteases followed by ultrafiltration optionally combined with diafiltration and ethanol precipitation of the resulting retentate. Alternatively, ethanol precipitation is directly executed with the ultrafiltrated retentate. In the best case the resulting refined AX product has a purity of at least 40% on dry matter in case diafiltration is combined with ethanol precipitation. In that case the compound still contains at least 10-15% protein resulting in a product with a compromised clarity and solubility if reconstituted in an aqueous solution. In addition the cost price for the resulting product is prohibitively high, because of enzyme cost and equipment required for multiple processing steps. In the present invention an economically feasible single step refining procedure is presented offering a facile way to reduce protein levels below 10-15% on d.m., to increase WS-AX content in excess of 40% and to improve sensory attributes like color and taste.

Figures 13, 14:
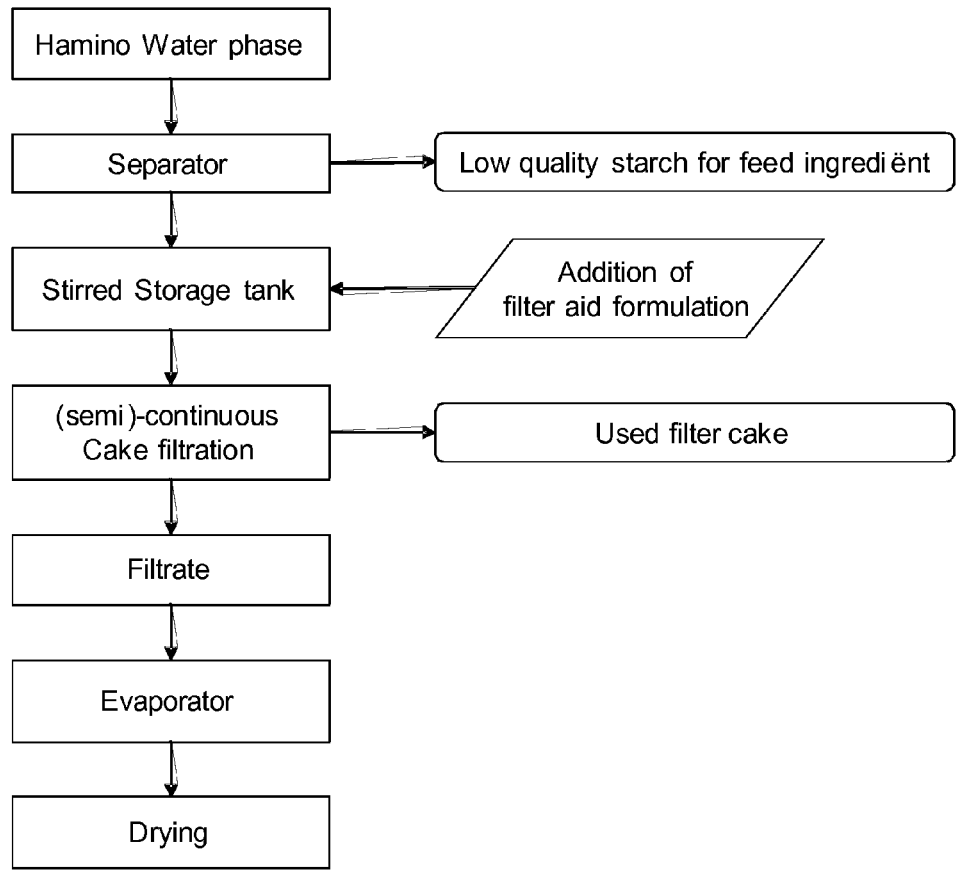
FIG. 13 Process flow diagram for improved soluble WS-AX.
FIG. 14 Composition of the WS-AX after cake filtration

In the improved refining procedure the combined refining treatments (including enzymatic treatments) have been replaced by a single cake filtration treatment using filter aid agents like cellulosic filter aids, perlite or diatomite optionally combined with activated carbon. Preferably the cake filtration unit operates an integrated cake washing program and automatic cleaning cycles. The process flow has been summarised in FIG. 13. Preferably, prior to the cake filtration the remaining starch content is reduced by a percentage of 20 to 40% by a centrifugal separator treatment. Subsequently the centrifuged Hamino is combined with a filter aid formula within a weight ratio of centrifuged Hamino to filter aid formula of 2:1 or more preferably 10:1 or even more preferably 100:1. The composition of the filter aid is for example a cellulosic filter aid, zeolite, perlite or diatomite mixed on a weight basis 1:0 up to 1:2 with activated carbon. Preferably a 1:0.1 (w/w) mixture of perlite and activated carbon is used and even more preferably a 1:0.05 (w/w) mixture of perlite and activated carbon is used. The de-starched Hamino fraction and filter aid mixture is passed over a caking filter installation allowing continuous or semi-continuous filtering at a 5T/hr scale or higher. A single washing of the cake is performed prior to removal. The exhausted cake material can optionally be heated to gelatinize the remaining starch in order to add value to this material for feed applications. Optionally, the resulting filtrate is further refined through a diafiltration treatment. The resulting (dia)filtrate is further concentrated using an evaporator and subsequently dried using a spray dryer or other drying technology like drum drying.

A quasi odorless, almost white product with good water solubility is obtained containing about 60%-85% WS-AX (w/w). The remaining fraction consists of low amounts of proteins and fat, and other carbohydrates (e.g. arabinogalactan and □-glucan) as summarised in the gross composition FIG. 14.

It is thus an object of the present invention to provide a water soluble arabinoxylan preparation containing as percentage on dry matter;

about 50%-90% of water soluble arabinoxylan, in particular about 55%-85%, more in particular about 60%;

up to about 1%, 2%, 3%, 4%, 5%, 6%, 7%, 8%, 9% or 10% of starch, in particular up to about 6%;

about 10%-30% of water soluble arabinogalactan, in particular about 15%-30%, more in particular about 25%;

about 0-5.0% of b-glucan; in particular about 1% of b-glucan;

about 0 to 1.0% of glucose; in particular about 0.5% of glucose;

about 1-10% of protein; in particular about 5% of protein; and about 0 to 1.0% of fat; in particular about 0.5% of fat.

A person skilled in the art will understand that the same process as described above can also be used for the extraction of long-chain soluble AX from the rest fraction of bioethanol production.

Accordingly, the present invention also provides any one of the aforementioned arabinoxylan preparations.

In a further aspect, it provides any one of the aforementioned arabinoxylan preparations for use as a medical, diet or clinical food or prophylactic agent for modulating or improving the intestinal microbial composition and/or the barrier, hormonal or immune function of the intestinal surface as described above, and/or for modulating or improving metabolic homeostasis, satiety, weight management, and/or for preventing the onset of cardiovascular diseases, all as described above.

Said method comprising the systemic or topical administration of an effective amount of said preparations, to animals, in particular warm-blooded animals, including mammals, i.e. humans.

The effective amount of a composition, according to the present invention, which is required to achieve a therapeutical effect will, of course, vary with the particular composition, the route of administration, the age and condition of the recipient, and the particular disorder or disease being treated. For a typical treatment a daily dosage of about 1.0 to 20.0 g; in particular of about 2.0 to 10.0 g; more in particular 5.0 g of the arabinoxylan preparations (supra) should be applied. For a typical person of 60-70 kg, this would require an intake of about 20-400 mg/kg per day of the arabinoxylan preparations (supra); in particular 40-100 mg/kg per day and more in particular 80 mg/kg per day.

Therefore, the compositions according to the invention would comprise between and about 0.5 g to 10.0 g of the arabinoxylan preparations as defined hereinbefore; in particular comprising between and about 1.0 g to 5.0 g of the arabinoxylan preparations per single unit dosage form.

As another aspect the present invention includes a combination of a composition as defined herein, with another agent for modulating or improving the intestinal microbial composition and/or the barrier, hormonal or immune function of the intestinal surface, and/or for modulating or improving metabolic homeostasis, satiety, weight management, and/or for preventing the onset of cardiovascular diseases, all as described above. as described above. Examples of such other agents are; (i) probiotics, such as for example selected from the non-limiting group consisting of *Bifidobacterium, Lactobacillus, Streptococcus, Enterococcus, Eubacterium, Clostridium* or *Saccharomyces* (ii) prebiotics, from the non-limiting group consisting of inulin, fructo-oligosaccharides or galacto-oligosaccharides.

While it is possible for the preparations to be administered alone, it is preferable to present them as a composition.

Compositions

It is also an object of the present invention to provide a composition for use in the methods of the present invention. The compositions can be prepared in any known or otherwise effective dosage or product form suitable for use in providing topical or systemic delivery of the arabinoxylan preparations, which would include both pharmaceutical dosage forms as well as nutritional product forms suitable for use in the methods described herein.

The compositions are preferably administered as oral dosage forms. Preferred dosage or product forms in this respect include oral tablets; capsules, including encapsulation in microcapsules or liposomes such as for example described in U.S. Pat. No. 5,827,531; instant formulas, oral liquids as well as bakery matrices such as bread, cookies and biscuits; and dairy products such as butter, cheese, milk and yoghurt.

The pharmaceutical and nutritional product forms are described hereinafter in greater detail. Another aspect of the invention is the topical use of the composition as a cosmetic, personal care or pharmaceutical application. Preferred dosage forms for this administration route are creams, gels or liquids.

Nutritionals

Generally, a nutritional or food composition according to the present invention comes as any form described in the present description, and in particular fat-based food products (butter, oil, margarine), bread, cookies, or oil kept food products, such as cheese, fish, meat, vegetables, or salads) or as seasoning products, such as condiments.

Especially, the compositions of the present invention come as liquid nutritional embodiments for oral or enteral administration that comprise one or more nutrients such as fats, carbohydrates, proteins, vitamins, and minerals. Oral liquid nutritionals are preferred for applications as medical, clinical or dietetic nutritional products, in particular as a beverage, for example a flavored beverage.

These nutritional liquids are preferably formulated with sufficient viscosity, flow, or other physical or chemical characteristics to provide a more effective and soothing coating of the affected mucosa while drinking or administering the nutritional liquid. These nutritional embodiments also preferably represent a balanced nutritional source suitable for meeting the sole, primary, or supplemental nutrition needs of the individual.

Non-limiting examples of suitable nutritional liquids within which the extracts can be formulated, and thus form selected nutritional liquid embodiments of the present invention, are dairy products such as milk and yoghurt; soy based 'dairy-like' products or a flavoured beverage.

Proteins suitable for use herein can be hydrolyzed, partially hydrolyzed or non-hydrolyzed, and can be derived from any known or otherwise suitable source such as milk (e.g. casein, whey), animal (e.g. meat, fish), cereal (e.g. rice, corn), vegetable (e.g. soy), or combinations thereof.

Fats or lipids suitable for use in the nutritional compositions include, but are not limited to, coconut oil, soy oil, corn oil, olive oil, safflower oil, high oleic safflower oil, MCT oil (medium chain triglycerides), sunflower oil, high oleic sunflower oil, structured triglycerides, palm and palm kernel oils, palm olein, canola oil, marine oils, cottonseed oils, and combinations thereof.

Carbohydrates suitable for use in the nutritional compositions may be simple or complex, lactose-containing or lactose-free, or combinations thereof. Non-limiting examples of suitable carbohydrates include hydrolyzed corn starch, maltodextrin, glucose polymers, sucrose, corn syrup, corn syrup solids, rice-derived carbohydrate, glucose, fructose, lactose, high fructose corn syrup and indigestible oligosaccharides such as fructo-oligosaccharides (FOS), and combinations thereof.

The nutritional compositions may further comprise any of a variety of vitamins, non-limiting examples of which include vitamin A, vitamin D, vitamin E, vitamin K, thiamine, riboflavin, pyridoxine, vitamin B12, niacin, folic acid, pantothenic acid, biotin, vitamin C, choline, inositol, salts and derivatives thereof, and combinations thereof.

A nutritional composition according to the present invention may further comprise minerals and trace elements such as sodium, potassium, phosphorus, magnesium, copper, zinc, iron, selenium, chromium and molybdenum.

Babyfood and Clinical Nutrition;

It was found that soluble arabinoxylans can be advantageously applied in baby food and clinical food. Such food preferably comprises lipid, protein and carbohydrate and can be administered in a liquid or solid form. The term "liquid food" as used in the present invention includes dry food (e.g. powders) that are accompanied with instructions as to admix said dry food mixture with a suitable liquid (e.g. water). Solid food includes food in the form of a supplement bar with a water activity between 0.2 and 0.4. Water activity can be defined as the ratio of the water vapour pressure of a product to the vapour pressure of pure water at the same temperature. The solid product must meet target water activity otherwise the product will not be shelf stable. Also semi-solid food and food-supplements are provided.

Hence, the present invention also relates to a nutritional composition that in addition to the present [arabinoxylans] preferably comprises between 5 and 50 en % lipid, between 10 and 60 en % protein, between 15 and 85 en % carbohydrate. In one embodiment the nutritional composition comprises between 15 and 50 en % lipid, between 25 and 60 en % protein and between 15 and 45 en % carbohydrate. In another embodiment the present nutritional composition comprises between 15 and 50 en % lipid, between 35 and 60 en % protein and between 15 and 45 en % carbohydrate.

Preferably lipids are used that have a high content of eicosapentaenoic acid (EPA) or linolenic acid (GLA). Fish oil and borage or evening primrose oil are preferred sources of these polyunsaturated fatty acids.

A source of digestible carbohydrate may be added to the nutritional formula. It preferably provides about 25% to about 40% of the energy of the nutritional composition. Any suitable (source of) carbohydrate may be used, for example sucrose, lactose, glucose, fructose, corn syrup solids, and maltodextrins, and mixtures thereof.

Preferably vitamins and minerals are present in amounts as required by FSMP regulations.

Pharmaceutical Compositions

The pharmaceutical compositions of the present invention can be prepared by any known or otherwise effective method for formulating or manufacturing the selected product form. Methods for preparing the pharmaceutical compositions according to the present invention can be found in "Remington's Pharmaceutical Sciences", Mid. Publishing Co., Easton, Pa., USA.

This invention will be better understood by reference to the Experimental Details and other specific examples that follow, but those skilled in the art will readily appreciate that these are only illustrative of the invention as described more fully in the claims that follow thereafter. Additionally, throughout this application, various publications are cited. The disclosure of these publications is hereby incorporated by reference into this application to describe more fully the state of the art to which this invention pertains.

EXAMPLES

The following examples illustrate the invention. Other embodiments will occur to the person skilled in the art in light of these examples.

Characterization of AX

Figure 1B:
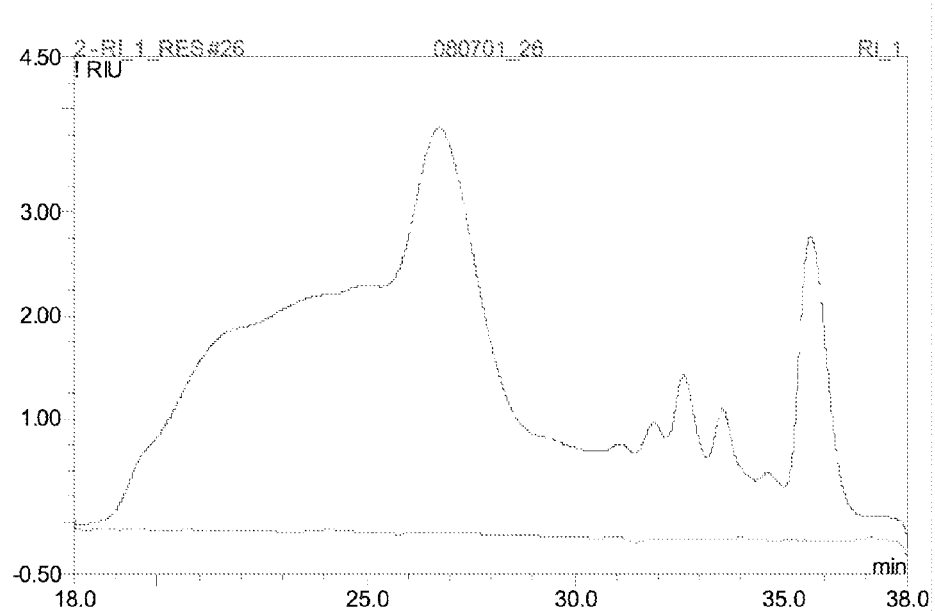
FIG. 1b High Performance Size Exclusion Chromatography (HPSEC) with pullulan calibration of a Naxus (AX) sample with Refractive Index (RI) detection.

Using High Performance Size Exclusion Chromatography (HPSEC) with pullulan calibration, a rather broad molecular weight distribution of Naxus was found ranging from 106 Da till monomer, with a rather large population in the range of 8-20 kDa (ca 8 kDa=ca DP60 and ca 20 kDa=ca 120 DP). (FIG. 1b). The presence of mono- and oligomers could indicate that the washing of the starting extract was not complete, but of note is that hardly any low molecular weight oligomers are eluting around and below 29 min. Using the alditol acetate method the Naxus sample was characterized for it sugar composition and it was found that arabinose (18% w/w) and xylose (25%) were the main sugars, next to low levels of galactose and glucose. The arabinose:xylose ratio (degree of substitution) was found to be 0.7 which is quite commonly found for wheat arabinoxylans. Next to all sugars present (total sugars:ca 56% w/w), about 22% proteins were present as based on the nitrogen content.

Measuring the sample according to Courtin et al (J. Chromatogr. A 866 (2000) 97-104) where the number of reducing end xylose residues was measured, it could be calculated that Naxus had (ON AVERAGE) 1 reducing end per 1743 xylose residues where 1743 represent the average degree of polymerization. The Degree of Polymerisation as based on both arabinose and xylose would be 1 reducing end on every 2963 residues.

High Performance Anion Exchange Chromatography (HPAEC) with PAD (pulsed amperometric detection) showed the presence of low amounts of xylose mono- and oligomers, next to more complex arabinoxylan oligosaccharides and maybe even glucuronoarabinoxylan oligomers.

To conclude, the water soluble AX is characterized in having a large high molecular weight fraction in the range of 8-20 kDA, with a high DP, a protein content of ca 22% (w/w) and a total sugar concentration of about 55% (w/w) mainly consisting of arabinose and xylose, i.e. mainly consisting of arabinoxylan.

Prebiotic Activities of AX

Experiment 1

In Vitro Gastrointestinal Model—the Simulator of the Human Intestinal Microbial Ecosystem (SHIME)

The reactor setup was adapted from the SHIME, representing the gastrointestinal tract of the adult human, as described by Molly et al. (Molly, Woestyne et al. 1993). The SHIME consists of a succession of five reactors simulating the different parts of the human gastrointestinal tract. The first two reactors are of the fill-and-draw principle to simulate different steps in food uptake and digestion, with peristaltic pumps adding a defined amount of SHIME feed (140 mL 3×/day) and pancreatic and bile liquid (60 mL 3×/day), respectively to the stomach (V1) and duodenum (V2) compartment and emptying the respective reactors after specified intervals. The last three compartments are continuously stirred reactors with constant volume and pH control. Retention time and pH of the different vessels are chosen in order to resemble in vivo conditions in the different parts of the gastrointestinal tract. The overall residence time of the last three vessels, simulating the large intestine, is 76 h. Upon inoculation with fecal microbiota, these reactors simulate the ascending (V3), transverse (V4) and descending (V5) colon. Inoculum preparation, retention time, pH, temperature settings and reactor feed composition were previously described by Possemiers et al. (Possemiers, Verthe et al. 2004). In the comparison with of AX with inulin, two systems with identical environmental conditions (identical pH and temperature control) were run in parallel.

Experiment Design:

Stabilization Period:

For the evaluation of the 2 prebiotics, the colon compartments of the SHIME reactors were first inoculated with an isolated fecal microbial community of a selected healthy volunteer. The SHIME reactor was operated under nominal conditions to stabilize the microbial community and let it adapt its metabolic activity and community composition to the conditions prevailing in the respective colon compartments. This stabilization period lasted for 3 weeks.

Basal Period:

During the basal period, the SHIME reactor was operated under nominal conditions. Parameters such as short chain fatty acid (SCFA) production and ammonium production were determined 3 times/week. The results of these analyses served as the background values to be used to compare the measured parameters from the treatment period. The basal period lasted 2 weeks.

Treatment Period:

During the treatment period, the SHIME reactor was operated under nominal conditions, but with a modified diet containing a lower amount of starch in the medium compared to that of the basal period. In parallel, the ascending colon compartment of the first SHIME received inulin, whereas the second SHIME received AX. Both compounds were added in low doses of 1.5 g/d. SCFA and ammonium production were determined 3 times/week. This treatment period typically lasts for 3 weeks.

Washout Period:

During the washout period, the SHIME reactor was operated under nominal conditions, with the initial diet. SCFA and ammonium production were determined 3 times/week. Analysis of these parameters allowed to assess whether possible changes from the treatment period normalize again to the levels of the basal period.

Outcome:

The results of the fatty acid analysis showed a superior prebiotic effect of AX compared to inulin. As acetate (A), propionate (P) and butyrate (B) are the main fatty acids produced by intestinal bacteria, the results are expressed as the ratio of each fatty acid to the sum of the 3 fatty acids. Prebiotic effects are characterized by a relative increase in P (cholesterol-lowering) and B (anti-proliferative) compared to A. Table 1 shows that such prebiotic effect was noted in each colon compartment of the SHIME treated with AX, whereas only minor effects were observed in one colon compartment in case of inulin.

TABLE 1

A, P and B ratios (e.g. A/(A + P + B)) in the different colon compartments of the TWINSHIME during control, treatment and wash-out period. Prebiotic effects are indicated by a decrease in A (italic) and increase of P and/or B (bold).

| | Ascending colon | | | Transverse colon | | | Descending colon | | |
|---|---|---|---|---|---|---|---|---|---|
| | A | P | B | A | P | B | A | P | B |
| INULIN | | | | | | | | | |
| Control | 0.44 | 0.27 | 0.29 | 0.43 | 0.31 | 0.26 | 0.52 | 0.25 | 0.22 |
| Treatment | 0.45 | 0.29 | 0.27 | 0.43 | 0.31 | 0.26 | *0.48* | 0.28 | 0.24 |
| Washout | 0.45 | 0.35 | 0.20 | 0.44 | 0.35 | 0.21 | 0.53 | 0.28 | 0.19 |
| AX | | | | | | | | | |
| Control | 0.48 | 0.33 | 0.18 | 0.47 | 0.36 | 0.17 | 0.52 | 0.33 | 0.15 |
| Treatment | *0.42* | 0.37 | 0.22 | *0.42* | 0.39 | 0.19 | *0.48* | 0.36 | 0.16 |
| Washout | 0.40 | 0.38 | 0.21 | 0.42 | 0.39 | 0.19 | 0.47 | 0.36 | 0.17 |

Experiment 2

Three groups of eight rats with human associated microbiotia were used in the experiment:
Control
Inulin
AX During three weeks animals were treated with either 10% inulin, AX or a control diet (=5% sugar+5% cornstarch) in order to compare the prebiotic effects of both oligosaccharides. At the end of the three weeks, the animals were euthanized.

Figure 2:
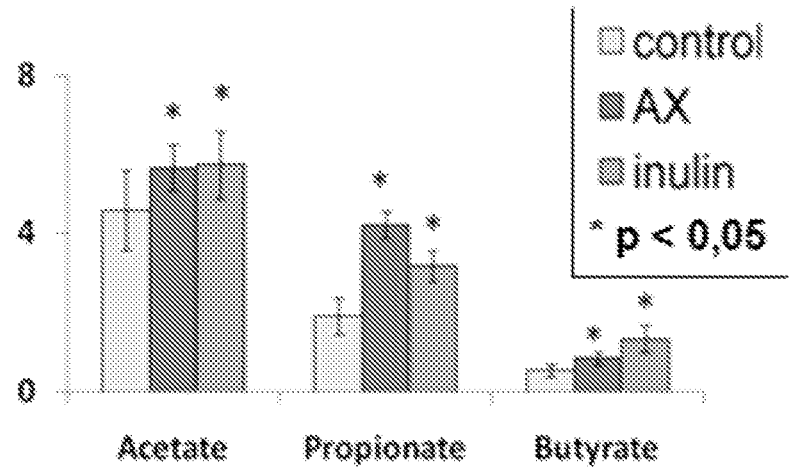
FIG. 2 Production of acetate, propionate and butyrate in the cecum of three groups of human-microbiota associated rats (n=8/group) treated for 3 weeks with a control diet, inulin (10%) or AX (10%).

FIG. 2 shows the results of the analysis of short-chain fatty acids in the cecum of the rats after the experiment. Whereas both treatments led to a moderate increase in propionate, acetate and butyrate, AX administration induced a more potent specific increase in propionate.

Figure 3:
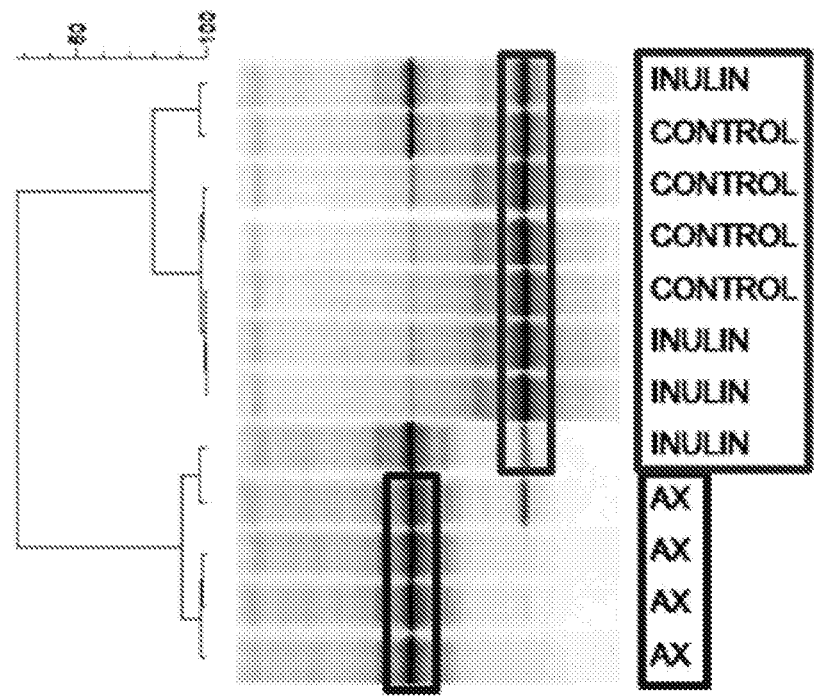
FIG. 3 DGGE (Denaturing Gradient Gel Electrophoresis) fingerprint profiles of the community of bifidobacteria in the cecum of three groups of human-microbiota associated rats (n=8/group) treated for 3 weeks with a control diet, inulin (10%) or AX (10%). The profiles were obtained after amplification of the bifidobacterial community using group-specific PCR primers.

In addition to this, the composition of the bifidobacterial community in the cecum was monitored by Denaturing Gradient Gel Electrophoresis (DGGE) (FIG. 3). Whereas little changes were observed in case of inulin, AX administration led to the appearance of a dominant *bifidobacterium*, identified as *Bifidobacterium longum*. *Bifidobacterium longum* is one of most important inhabitants in the human body. This bacterium is very helpful because it maintains a normal digestive tract, inhibits the growth of harmful bacteria, and also boosts the immune system (Reinert, Birgit. "Friendly tenants in the human gut: The genome of *B. longum*". 2002. Genome News Network).

Mucosal Barrier Activities of AX

In addition to the above-mentioned measurements, experiments were performed to quantify the attachment of intestinal bacteria to the mucus layer at the gut wall. As attachment to the gut wall is the first stage of interaction between bacteria and the human host (e.g. immunomodulation, pathogenesis), characterization of the microbial ecology at the site of the gut wall and assessment of changes in this community due to a prebiotic treatment is very important to evaluate the final health effects of a prebiotic treatment. Finally, the effect of the prebiotic treatment with inulin or AX on the composition of the microbial community in both the gut lumen and at the gut wall can be expressed quantitatively in specific indices.

The Prebiotic Index (PI) describes the increase in the gut lumen in beneficial bacteria, relative to harmful bacteria due to the prebiotic treatment.

PI=(Bif/Total)+(Lac/Total)−(Ecol/Total)−(Clos/Total)

The Prebiotic Attachment Index (PAI) describes the increase at the site of the gut wall in beneficial bacteria, relative to harmful bacteria due to the prebiotic treatment.

PAI=(Bif/Total)+(Lac/Total)−(Ecol/Total)−(Clos/Total)

Figure 4:
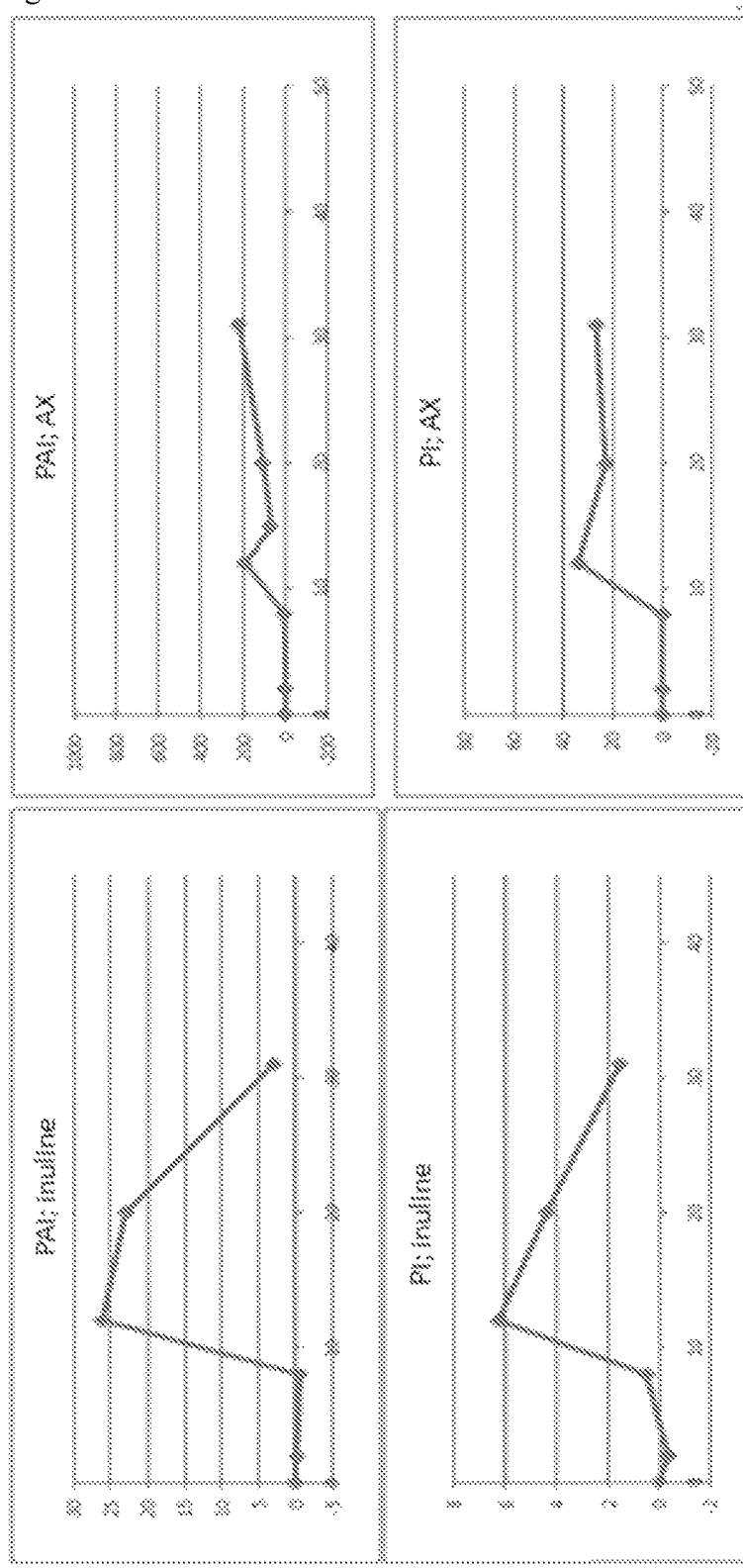
FIG. 4 Prebiotic Index (PI) and Prebiotic Attachment Index (PAI) before, during and after treatment with respectively inulin and AX. The X-axis indicates experiment days during the TWINSHIME run. Inulin or AX were administered to the TWINSHIME from day 2 until day 23.

For both indices, an increase in the quantitative value is evaluated as positive, with the degree of increase as a parameter for success of the prebiotic treatment (FIG. 4). Comparison of the PI and PAI for inulin and AX again shows a superior prebiotic effect of AX. Both the PI and PAI increased at least 5-fold more for AX, and whereas the PI and PAI returned back to baseline for inulin after stopping the administration (from day 23), both indices remained high for AX.

Effect of AX in the Development Obesity Induced by High Fat Diet in Mice

Experiment Design:

For the evaluation of the development of obesity, C57bl6/j mice were fed a control normal-chow diet (CT, n=8) or a Westernized high fat diet (HF, n=8), supplemented or not with AX (HF-NX, n=8) (10 g/100 g of diet) for 4 weeks.

Figure 5:
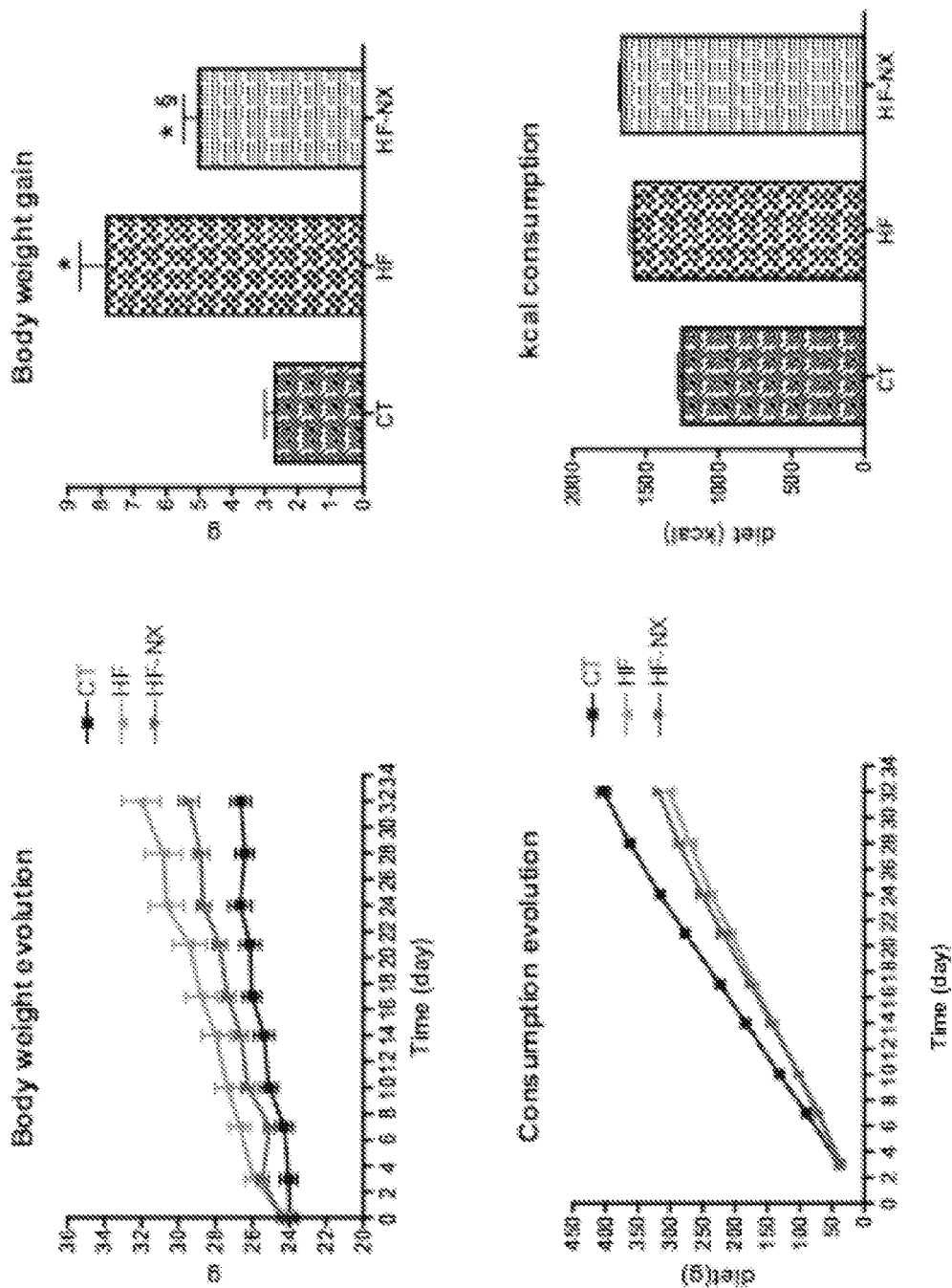
FIG. 5 Effects on body weight and consumption in C57bl6/j mice fed with a control normal-chow diet (CT, n=8) or a high fat diet (HF, n=8), supplemented or not with AX (HF-NX, n=8) (10 g/100 g of diet) for 4 weeks. * p<0.05 versus CT, §p<0.05 versus HF.
Figure 6:
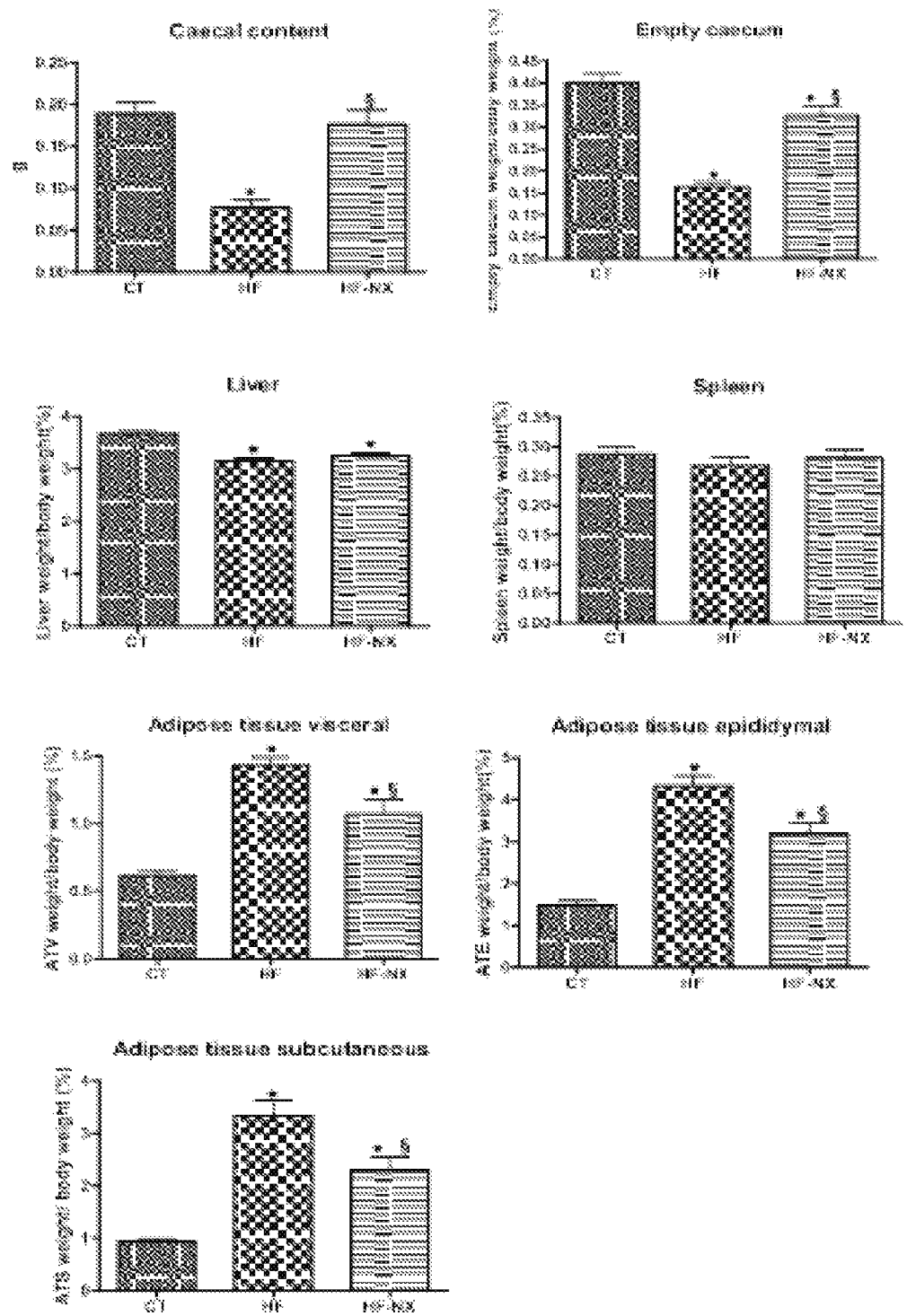
FIG. 6 Effects on Organ Weight (Caecal content, Liver, Spleen, Adipose Tissue (visceral, epididymal, subcutaneous)) in C57bl6/j mice fed with a control normal-chow diet (CT, n=8) or a high fat diet (HF, n=8), supplemented or not with AX (HF-NX, n=8) (10 g/100 g of diet) for 4 weeks. * p<0.05 versus CT, §p<0.05 versus HF.
Figure 7:
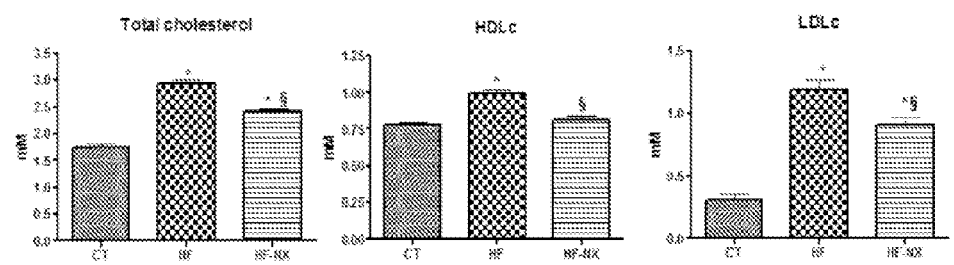
FIG. 7 Effects on total, LDL and HDL cholesterol in C57bl6/j mice fed with a control normal-chow diet (CT, n=8) or a high fat diet (HF, n=8), supplemented or not with AX (HF-NX, n=8) (10 g/100 g of diet) for 4 weeks.

Several parameters were assessed during and after 4 weeks of treatment:
Changes in body weight and increase of adipose tissue
Food intake
Fermentation: ceacal enlargement
Lipid homeostasis (triglycerides, non-esterified fatty acids, cholesterol) in serum and liver tissue Results:
  Addition of AX (10%) in the HF diet induced:
    BW gain, independently of energy intake (food consumption) (FIG. 5). Although the HF-NX mice consumed similar daily amounts of calories as the HF mice, body weight gain was significantly lower compared to the HF mice. This showed that AX exerts protective effects on body weight gain and weight management.
    adiposity (weight of adipose tissues) (FIG. 6). AX administration led to significantly lower fat deposition in the epididymal, subcutaneous and visceral adipose tissue, when compared to high fat diet.
    induced cecal fermentation (cecal content and tissue weight versus HF group) (FIG. 6).
    Lowering of total, LDL and HDL cholesterol (FIG. 7).

Protective Effect of AX Towards High-Fat Diet and Obesity Related Changes in the Gut Microbial Community C57bl6/j mice were fed a control normal-chow diet (CT, n=8) or a Westernized high fat diet (HF, n=8), supplemented or not with AX (HF-NX, n=8) (10 g/100 g of diet) for 4 weeks.

Changes in the composition of the gut microbial community in mice were assessed by sampling of fresh cecum content upon killing the animals. Concentrations of total bacteria, bifidobacteria, bacteroides-prevotella and Cluster XIVa of clostridia were assessed by specific qPCR protocols.

Figure 8:
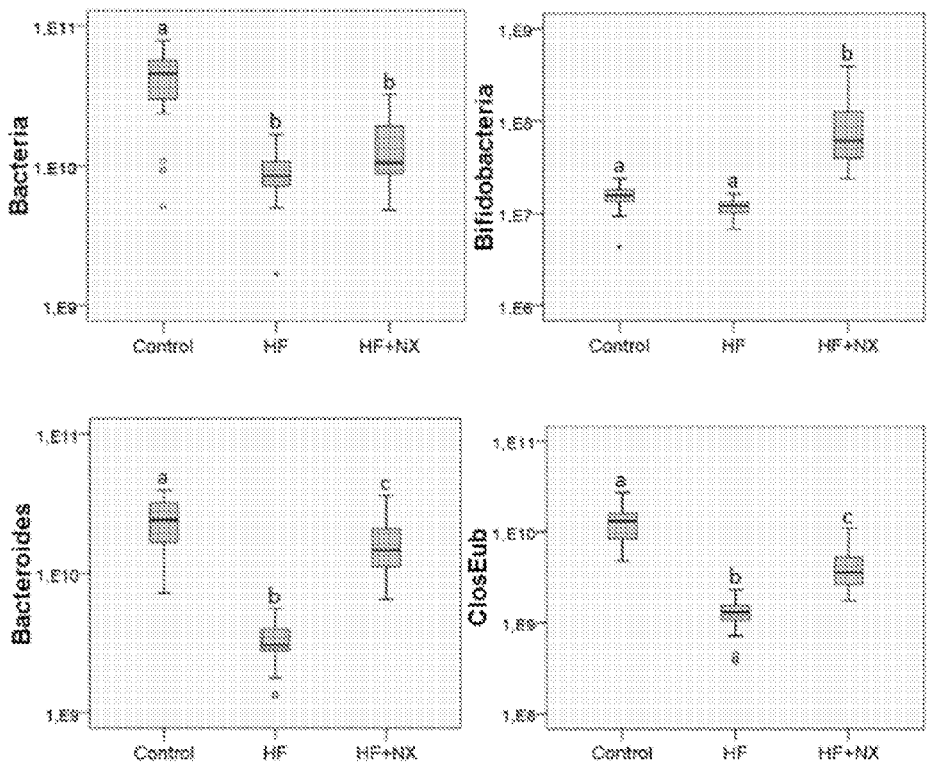
FIG. 8 Changes in the counts (16S rDNA copies/total cecum content) of specific bacterial groups as detected by qPCR. 3 groups of C57bl6/j mice were administered normal-chow diet (CT, n=8) or a high fat diet (HF, n=8), supplemented or not with AX (HF-NX, n=8) (10 g/100 g of diet) for 4 weeks.

FIG. 8 shows that high-fat induced obesity includes drastic changes in microbial community composition in the cecum. Combination of a high-fat diet with AX however, restored most changes in the community composition and induced significant increase in counts of bifidobacteria, confirming the potent selective prebiotic activity towards bifidobacteria. As a decrease in specifically the counts of bacteroides has been related with obesity, restoration of the counts of this group by AX can be seen as an important factor in the protective effects of AX towards weight management.

Immune-Modulatory Effect of AX Towards the Local and Systemic Immune System

C57bl6/j mice were fed a control normal-chow diet (CT, n=8) or a Westernized high fat diet (HF, n=8), supplemented or not with AX (HF-NX, n=8) (10 g/100 g of diet) for 4 weeks.

Changes in the local and systemic immune functioning were assessed by respectively assessing the functioning of the gut barrier capacity (e.g. involved in leakage of bacterial antigens such as LPS and translocation of pathogens) and immune parameters in the serum (pro- and anti-inflammatory cytokines and chemokines).

Figure 9:
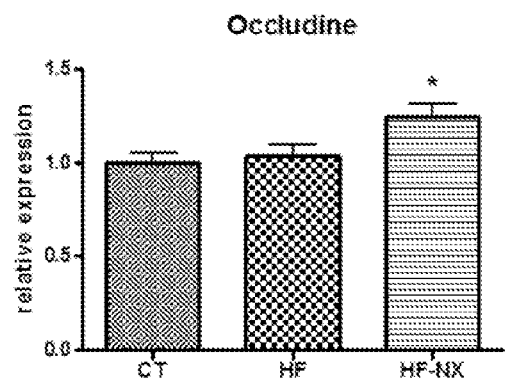
FIG. 9 Effect on occludine mRNA expression in the ileum in C57bl6/j mice fed with a control normal-chow diet (CT, n=8) or a high fat diet (HF, n=8), supplemented or not with AX (HF-NX, n=8) (10 g/100 g of diet) for 4 weeks.

FIG. 9 describes changes in the expression of occludine mRNA in the ileum. Occludine is a marker for intestinal barrier functioning, a crucial aspect of the local immune functioning in the gut. An increase in occludine mRNA is correlated with improved barrier functioning of the gut immune system. Administration of AX significantly increased the occludine mRNA content, indicating improved functioning of the local immune system upon ingestion of AX.

Figure 10:
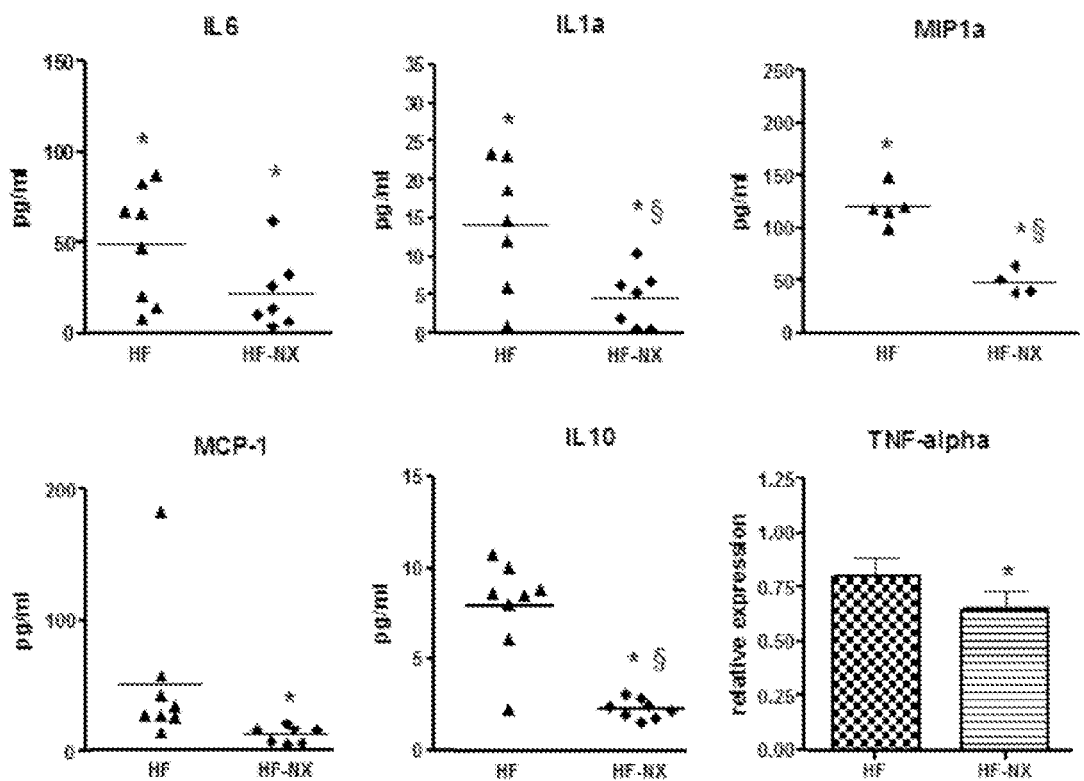
FIG. 10 Effects on circulating inflammation mediators in the blood (IL6, IL1a, MIP1a, MCP-1 and IL10) and on liver TNFalfa mRNA expression in C57bl6/j mice fed with a control normal-chow diet (CT, n=8) or a high fat diet (HF, n=8), supplemented or not with AX (HF-NX, n=8) (10 g/100 g of diet) for 4 weeks.

FIG. 10 describes the concentrations of circulating (in the blood) inflammatory mediators and the TNFalfa expression in the liver. Administration of AX led to a significant decrease of the general inflammation status of the animals, with a lowering of both pro- and anti-inflammatory cytokines. Further indications of systemic immune-modulation upon AX administration were obtained by a significant decreased liver TNFalfa mRNA expression.

Effect of AX Towards Prevention of Cardiovascular Disease

The preventive effect of AX consumption towards CVD was assessed by the evaluation of the changes in two highly important causal risk factors of CVD, i.e. oxidative stress and chronic inflammation.

To do this, C57bl6/j mice were fed a control normal-chow diet (CT, n=8) or a Westernized high fat diet (HF, n=8), supplemented or not with AX (HF-NX, n=8) (10 g/100 g of diet) for 4 weeks.

Protection against oxidative stress was assessed by monitoring of liver TBARS (liver thiobarbituric acid reactive substances) and NADPH oxidase.

TBAR concentrations are an index of lipid peroxidation and oxidative stress and a decrease is therefore a marker for a decrease in oxidative stress. NADPH oxidase is a major cause of atherosclerosis, and NADPH oxidase inhibitors may reverse atherosclerosis. Atherosclerosis is caused by the accumulation of macrophages containing cholesterol (foam cells) in artery walls. NADPH oxidase produces reactive oxygen species (ROS). These ROS activate an enzyme that makes the macrophages adhere to the artery wall (by polymerizing actin fibers). This process is counterbalanced by NADPH oxidase inhibitors, and by antioxidants.

Figures 11, 12:
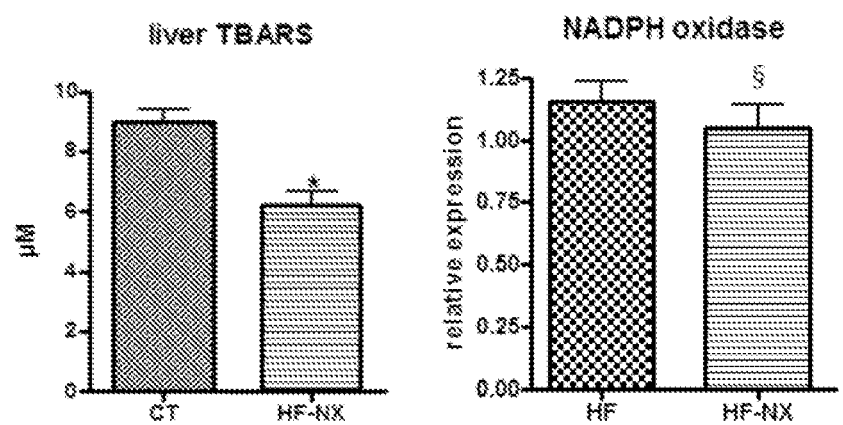
FIG. 11 Effect on liver TBAR concentrations and NADPH oxidase mRNA expression in C57bl6/j mice fed with a control normal-chow diet (CT, n=8) or a high fat diet (HF, n=8), supplemented or not with AX (HF-NX, n=8) (10 g/100 g of diet) for 4 weeks. * p<0.05 versus CT, §p<0.05 versus HF.
FIG. 12 Composition of the aqueous phase (Hamino) of a three phase decanter separation step in wheat starch manufacturing.

FIG. 11 shows that AX significantly decreased TBAR concentrations in the liver of HF-NX mice, as compared to the control mice, indicating a decrease in oxidative stress upon AX consumption. In addition, elevated NADPH oxidase expression in the liver of HF mice was counteracted by AX administration, as shown by the decreased expression in HF-NX mice, which indicates protection against oxidative stress by AX.

AX administration led to a significant decrease of the general inflammation status of the animals, with a lowering of both pro- and anti-inflammatory cytokines and of liver TNFalfa mRNA expression, indicating protection against chronic inflammation (FIG. 10).

Finally, AX treatment also protected against other typical established risk factors for CVD, i.e. lowering of LDL cholesterol (FIG. 7) and protection against weight gain (FIG. 5). Though protection against one particular risk factor of CVD is useful, it is now widely accepted that CVD is a multi factorial disease and that prevention and/or treatment preferably addresses more than one risk factor, whereby oxidative stress and/or chronic inflammation are the more fundamental risk factors that should be addressed in any case.

Exemplary Nutritional Compositions

Dairy Products

Dairy trails will be carried out to obtain food products with physiologically relevant levels of the preparations according to the invention, demonstrating a sensory appreciated end product with comparable or superior shelf life when compared to the non-formulated extracts.

Physiologically relevant levels are expected to be between and about 0.1 and 10 g of arabinoxylans per serving; in particular between and about 1 to 5 g of arabinoxylans per serving.

Dairy products are milk and products made from milk, including cheese, butter and yoghurt. In a particular embodiment the dairy composition will be based on yoghurt where the arabinoxylan preparations of the present invention will be added at the different levels mentioned hereinbefore and at different steps during the production process.

In a particular embodiment the food compositions, in particular the dairy products further comprise a probiotic, such as for example selected from the non-limiting group consisting of *Bifidobacterium, Lactobacillus, Streptococcus, Enterococcus, Eubacterium, Clostridium* or *Saccharomyces*.

Bakery & Dietetic Products

Two different bakery matrices will be tested covering two major segments of the bakery and dietetic market, i.e. bread (white flour based) and bars (savoury and sweet).

The arabinoxylan preparations will be added at different levels during dough mixing and before proofing. For each recipe 20 breads and three batches of biscuits will be baked. The resulting breads will be assessed for their loaf volume, crumb structure, taste and staling stability. The bar will be assessed for their oxidation stability (rancimat test) and sensory attributes.

In order to give a physiological effect, bakery compositions are expected to comprise between and about 0.1 and 12 g of arabinoxylans per serving; in particular between and about 1 to 5 g of arabinoxylans per serving.

Infant Nutrition Products

A first example of an infant nutrition product is a powdered infant formula, which can be reconstituted with water (15.6 g powder per 100 ml final volume) comprising per 100 ml ready to use product:
Protein source: 1.9 g
Fat: 3.3 g
Digestible carbohydrates: 8.7 g
Non-digestible fermentable carbohydrate: 0.8 g (NAXUS, BioActor)
Hydrolysed whey, hydrolysed casein in a weight ratio 6/4

Another example of infant nutrition is a drink, comprising per 100 ml 67 kcal and:
1.9 g protein:
3.0 g fat: (0.75 g milk fat; 1.95 g high oleic sunflower oil/canola oil mixture; 0.3 g corn oil)
8.11 g digestible carbohydrates: (7.8 g lactose, 0.22 glucose; 0.01 galactose; 0.01 polysaccharides; 0.06 organic acids)
0.8 g water soluble arabinoxylans (NAXUS from BioActor)
micronutrients: 0.89 mg zinc; 2.3 [mu]g Se; 65 [mu]g-RE vitamin A of which 24.6 [mu]g-

Clinical Nutrition Products specific illustrative composition of a dry mix to be dissolved in a drinkable liquid such as water or milk are provided below:
Flavor: Lemon
Ingredient g/unit dose (serving)
malic acid 1.0
lemon flavoring 0.1
citric acid 2.5
acesulfame-k 0.04
aspartame 0.05
a-tocopherol 0.3
ascorbic acid 0.5
FD & C yellow 0.0003
Soluble arabinoxylans 2.5 g (NAXUS, BioActor)

The invention claimed is:

1. A method of modulating a function of an intestinal surface with a preparation containing a water-extractable arabinoxylan (AX) fraction produced from wheat comprising isolated water-soluble arabinoxylans with an average degree of polymerization of at least 60 to modulate barrier function of the human intestinal surface, the hormonal functioning of the intestinal surface, functioning of the local and/or systemic immune system, metabolic homeostasis, or a combination thereof comprising: feeding a human said preparation.

2. The method according to claim 1, wherein said preparation modulates the barrier function of the intestinal surface including:
   stimulating growth and/or activity of one or a limited number of beneficial bacteria in the intestinal tract;
   inhibiting growth and/or activity of one or a number of pathogenic bacteria in the intestinal tract;
   relatively increasing the attachment of non-pathogenic bacteria to the mucosa of the gastrointestinal surface;
   reducing uncontrolled uptake from the gut of antigens, pro-inflammatory molecules, bacteria or bacterial products;
   providing anti-inflammatory activity at the intestinal surface;
   producing specific bacterial metabolites, or a combination thereof.

3. The method according to claim 2, wherein the preparation causes a relative increase of beneficial bacteria at the intestinal surface.

4. The method according to claim 2, wherein the preparation causes a relative decrease of pathogenic bacteria at the intestinal surface and/or a reduction in translocation of pathogenic bacteria from the gastrointestinal tract.

5. The method according to claim 2, wherein the preparation causes a reduction in translocation antigens, pro-inflammatory molecules, bacteria or bacterial products from the gut.

6. The method according to claim 2, wherein the preparation causes anti-inflammatory activity at the intestinal surface.

7. The method according to claim 2, wherein the preparation leads to improved functioning of the local and/or systemic immune system.

8. The method according to claim 2, wherein the preparation leads to improved metabolic homeostasis, induction of satiety, improved weight management, or a combination thereof.

9. The method according to claim 1 wherein said water extractable arabinoxylan (AX) fraction produced from wheat comprises isolated water-soluble arabinoxylans with an average molecular weight fraction of at least 8 kDa; a degree of substitution of between 0.4 and 0.9; a protein content of up to about 22 wt %; and a total sugar concentration of at least 55 wt %.

* * * * *